United States Patent [19]

Tansamrit et al.

[11] Patent Number: 5,045,164
[45] Date of Patent: Sep. 3, 1991

[54] ELECTROPHORESIS PLATE FOR DIVERTING GENERATED FLUID

[75] Inventors: Aungnapa Tansamrit; Subphong Tansamrit, both of Beaumont, Tex.

[73] Assignee: Helena Laboratories Corporation, Beaumont, Tex.

[21] Appl. No.: 527,358

[22] Filed: May 23, 1990

[51] Int. Cl.$^5$ ..................... G01N 27/26; B01D 57/06
[52] U.S. Cl. .............................. 204/182.8; 204/180.1; 204/299 R
[58] Field of Search .............. 204/180.1, 182.8, 299 R

[56] References Cited

U.S. PATENT DOCUMENTS

| 3,674,678 | 7/1972  | Post            | 204/299 R |
| 3,773,646 | 11/1973 | Mandle          | 204/299 R |
| 4,415,418 | 11/1983 | Turre et al.    | 204/182.8 |
| 4,417,967 | 11/1983 | Ledley          | 204/182.8 |
| 4,874,491 | 10/1989 | Stalberg        | 204/182.8 |
| 4,883,577 | 11/1989 | Sugimoto et al. | 204/182.8 |
| 4,892,639 | 1/1990  | Sarrine         | 204/299 R |
| 4,975,173 | 12/1990 | Tansamrit       | 204/299 R |

FOREIGN PATENT DOCUMENTS

87/04948  8/1987  PCT Int'l Appl. .
89/00689  1/1989  PCT Int'l Appl. .

Primary Examiner—T. Tung
Assistant Examiner—David G. Ryser
Attorney, Agent, or Firm—Spencer & Frank

[57] ABSTRACT

An improved electrophoresis plate of the type including a base layer of an electrophoretic medium and opposed thickened ends made of an electrophoretic medium containing a desired fluid, such as a buffer material or solvent. The thickened ends function as a self-contained reservoirs during electrophoresis. The thickened ends of the present invention divert water generated by electroendosmosis or gel melt away from the electrophoresis area. This may be accomplished by providing a hollow region within the thickened ends which holds the water generated. Alternatively, serrations on the edges of the plate, or on the edges of the thickened ends of the plate which are disposed away from the electrophoresis area, may be provided to act as a path by which the water generated can flow away from the electrophoresis area.

12 Claims, 2 Drawing Sheets

ELECTROPHORESIS PLATE FOR DIVERTING GENERATED FLUID

CROSS-REFERENCE TO RELATED APPLICATION

The present application is related to the invention of an Electrophoresis Plate and Method of Making Same as described in the copending application of Tansamrit, et al., filed Feb. 22, 1989, as application No. 07/313,764, and assigned to the assignee of the present invention. The disclosure of the aforementioned application is incorporated by reference.

BACKGROUND OF THE INVENTION

The present invention relates to improvements in electrophoresis plates. By way of background, electrophoresis is a well-established method for separation of charged macromolecules or colloidal particles and is useful in the analysis of proteins found in complex physiological fluids and tissue. Typically, electrophoresis is carried out in a separation medium, for example a polymer gel, such as agarose or polyacrylamide. Of course, cellulose acetate is also used as a separation medium.

In the formation of an electrophoresis plate, the electrophoretic or polymer gel is cast in a mold and secured to an inert substrate. In the electrophoresis process, numerous samples are typically placed on the electrophoretic medium, i.e., the polymer gel. To effect electrophoretic separation, an electric field is established with respect to the gel containing the samples.

Various fluids may be added to the gel during the electrophoretic separation, such as solvent or buffer. When providing fluid to the plate for the electrophoretic process, different means have allowed fluid to be delivered at one end of the plate and removed from the other. For example each end of the electrophoresis plate has been put into separate reservoirs. Alternatively fluid has been allowed to wick onto and off of opposite ends of the plate from separate reservoirs.

U.S. Pat. No. 4,892,639 describes another approach to delivering fluids to an electrophoresis plate by providing thickened regions at the respective ends of the plates. The thickened regions are made of the polymer gel and include a quantity of the fluid, e.g. buffer, to be delivered to the plate. This approach advantageously results in a self-contained electrophoresis plate.

During the electrophoretic process, certain phenomenon occur which may interfere with or adversely influence the electrophoretic separation, especially for electrophoresis plates having thickened ends. For example, a heat build-up is associated with the voltage gradient which develops during the process, causing water which is present in the gel to become more mobile and to flow. If there is excessive fluid flow, called electroendosmotic (EEO) flow, water is delivered to the electrophoresis plate from the thickened ends, with a blurring and broadening of the electrophoresis zones thus contaminating the electrophoresis zone and interfering with the analysis of the electrophoresed sample. Another problem which occurs as a result of heat build-up is the actual collapse of the thickened ends of the plate, which is referred to as gel melt. These are problems with typical commercial agarose gel media. Gel melt may even occur when a thin layer of agarose gel is placed on a substrate and electrophoretic separation is performed using the aforementioned wicking approach to add fluid to the plate without the use of buffer blocks.

The present invention provides a solution to these problems pertaining to electrophoresis plates, as will be hereinafter described.

SUMMARY OF THE INVENTION

The present invention provides an improved electrophoresis plate of the type including a base layer of an electrophoretic medium and preferably including two opposing thickened ends made up of an electrophoretic medium containing a desired fluid, such as a buffer material. The thickened ends function as a self-contained reservoirs during electrophoresis. Means are provided, preferably as part of the thickened ends of electrophoretic medium, for diverting water generated by electroendosmosis away from the electrophoresis zone. The means for diverting water away from the electrophoresis zone can be a hollow region within the thickened ends which holds the water generated. Alternatively, the means for diverting water away from the electrophoresis plate can be serrations at the edge of the plate or at the edges of the thickened ends which are disposed away from the electrophoresis plate. The serrations act as paths along which the water can flow.

BRIEF DESCRIPTION OF THE DRAWINGS

A better appreciation of the invention, and its attendant advantages, should result from the following detailed description and the accompanying drawings, wherein.

DETAILED DESCRIPTION OF THE PREFERRED EMBODIMENTS

Figure 1:
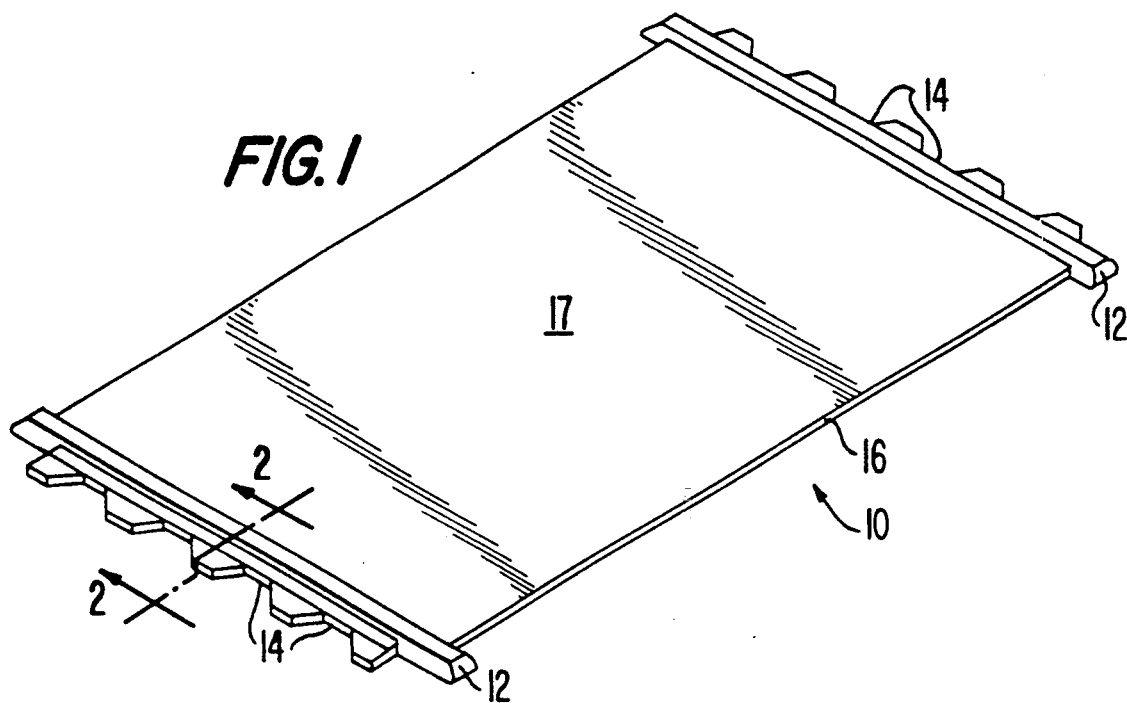
FIG. 1 is a perspective view of an electrophoretic medium according to the present invention.

FIG. 1 shows a generally rectangular electrophoretic medium 10. The electrophoretic medium 10 is illustrated as a generally rectangular planar layer having thickened ends 12. Thickened ends 12 are disposed on the lateral ends of a planar electrophoretic layer 16 which are perpendicular to the longitudinal axis of the rectangular medium. An electrophoresis area o zone 17 is defined as the region between the thickened ends. In the embodiment shown in FIG. 1, serrations or teeth 14 are provided on the edges of the thickened ends which face away from the electrophoresis area 17.

Figure 2:
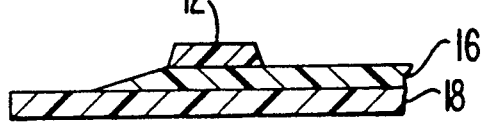
FIG. 2 is a cross-sectional view of the electrophoretic medium along line 2—2 of FIG. 1 disposed on a substrate.

FIG. 2 shows a cross-sectional view of the medium along line 2—2 from FIG. 1 disposed on a substrate 18. Thickened end 12 is positioned on planar electrophoretic layer 16. These two, which make up the electrophoretic medium 10, are then positioned upon a planar substrate 18.

The electrophoresis plate according to the invention includes a substrate 18 of a substance which is both electrically and chemically inert. The substrate may be selected from one of many materials that are conventionally used as supports for electrophoretic gel media and have the desired degree of rigidity to support and protect the gel from damage during handling and shipment. Film materials that are suitable for this purpose include polystyrene, polyethylene and glass, as well as polyesters. A preferred substrate is a polyester film sold by E.I. du Pont de Nemours and Company under the trademark Mylar. An alternative substrate which is equally satisfactory is a thermoplastic polycarbonate film sold by General Electric under the trademark Lexan.

In the following discussion, it will be assumed that agarose gel is used as the electrophoretic medium. However, it should be understood that according to the principles of the present invention, other electrophoretic media may be used. This includes, without limitation, the use of polyacrylamide whether cross-linked or not, regardless of whether a catalyst is present.

According to the present invention, the electrophoretic planar layer 16 may be 0.016 inches thick, and the thickened ends should be between about 0.0100 to about 0.0150 inches thick, in addition to the thickness of the planar layer 16. Of course these dimensions are illustrative as to the relative size of the layers according to the preferred embodiment of the invention, and should not be interpreted as a limitation of the present invention.

Figure 3:
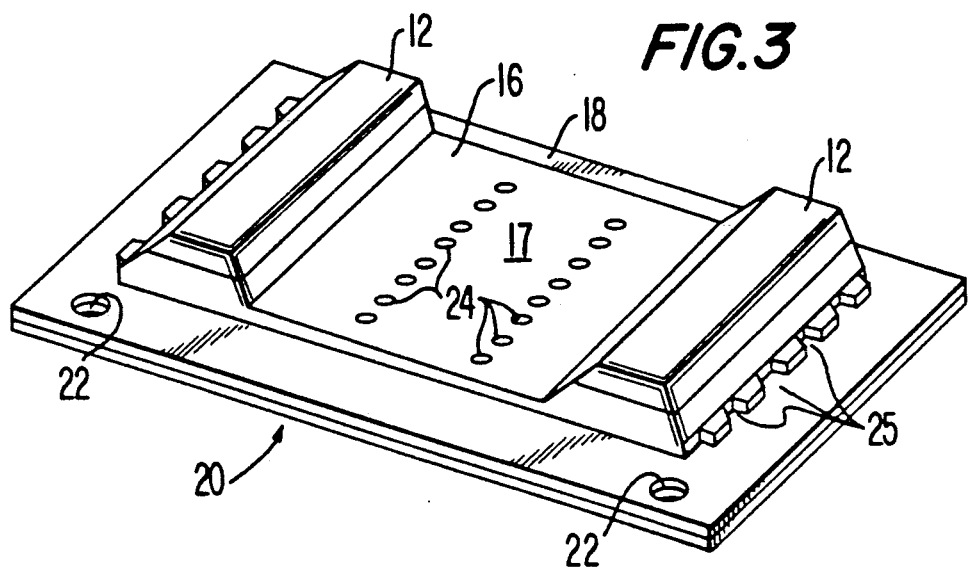
FIG. 3 is a perspective view of an electrophoresis plate using the medium of FIG. 1.

FIG. 3 shows an electrophoresis plate 20 according to an embodiment of the present invention. Electrophoretic medium 10 of FIG. 1 is disposed on substrate 18. Thickened ends 12 are provided on the electrophoresis plate 20 such that they are perpendicular to the electric field used for electrophoresis. Alignment holes 22 are used to align the plate properly to electrodes, not shown, which generate the electric field used in the electrophoretic separation. Additionally, alignment holes 22 may be used in positioning the substrate for proper placement of the thickened ends on the electrophoretic planar layer 16.

Figure 4:
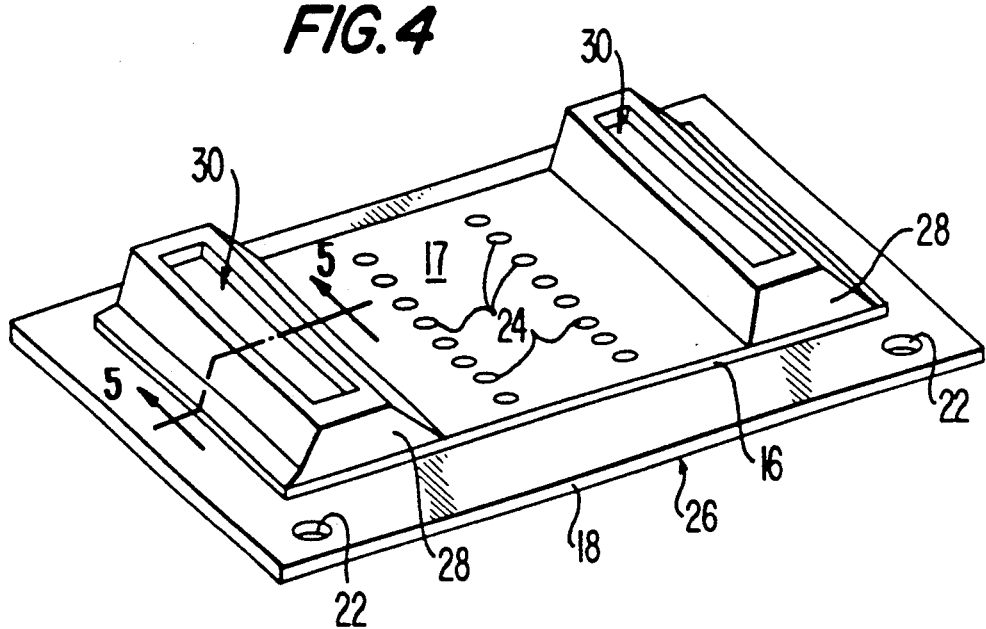
FIG. 4 is a perspective view of another embodiment of an electrophoresis plate according to the present invention.

The planar electrophoretic layer 16 may also be provided with a series of sample apertures 24. As seen in FIGS. 3 and 4, two series or rows of apertures are provided. The sample apertures are aligned to be perpendicular to the elongated axis of the plate 20 and parallel to the elongated axes of the thickened ends 12.

Should the thickened ends start to melt for any reason, such as the heat generated during the electrophoretic process, serrations divert water, from any source, such as that dissociated from the agarose gel or from the buffer, away from the electrophoretic zone or area 17. This keeps such water from blurring the electrophoretic separation. In FIG. 1 serrations 14 are illustrated as formed in the thickened end 12 while in FIG. 3 serrations 25 are illustrated as formed in the planar layer 16.

FIG. 4 shows another embodiment of an electrophoresis plate 26 according to the present invention. Here the electrophoretic medium includes a electrophoretic planar layer 16 made of a polymer gel, e.g. agarose, and thickened ends 28 disposed perpendicularly to the longitudinal axis of planar electrophoretic planar layer 16 on its lateral ends. Comparably to the embodiment described in FIG. 3, electrophoresis plate 26 has electrophoretic medium 16 disposed on substrate 1B, alignment holes 22, and sample apertures 24 disposed on the electrophoresis zone or area 17.

Figure 5:
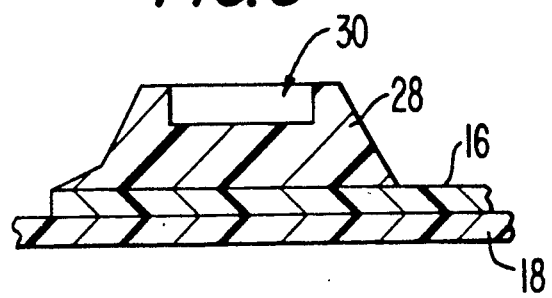
FIG. 5 is a cross-sectional view along line 5—5 of FIG. 4.

FIG. 5 is a cross-section view along line 5—5 of FIG. 4. As seen in FIGS. 4 and 5, hollow area 30 is provided in thickened end 28. Should the thickened ends start to melt during the electrophoresis process, hollow area 30 allows water which may become disassociated from the agarose gel to accumulate. This diverts such water from flowing onto the planar electrophoretic area 17, with associated blurring of the electrophoretic separation.

Due to the use of a fluid diverting means to control the problem of water flow onto the electrophoresis plate, the present invention provides a particularly economical way of overcoming this problem.

Although the fluid diverting means has been illustrated in two embodiments, it should be appreciated that further embodiments are contemplated by the present invention. For example, serrations or notches may be provided in the base gel layer itself. The hollow portions of the thickened ends may extend through the ends and even be connected to an external drain.

The foregoing is a complete description of preferred embodiments of the invention. Various changes may be made without departing from the spirit and scope of the present invention. The invention, therefore, should be limited only as set forth in the claims.

What is claimed is:

1. In a process of electrophoretic separation using an electrophoresis plate having a planar layer comprising an electrophoretic medium, the electrophoretic medium including at least some fluid, and a thickened portion provided on two opposing ends of said planar layer, forming an electrophoresis area between the two thickened portions, each of said thickened portions having an edge facing away from the electrophoresis area and including the electrophoretic medium and fluid, the thickened portion functioning as a self-contained fluid reservoir for electrophoresis, the improvement comprising:

diverting water separated during electrophoresis away from the electrophoresis area.

2. A process of electrophoretic separation as defined in claim 1, wherein the step of diverting water away from the electrophoresis area includes providing a hollow portion in the thickened portions.

3. A process of electrophoretic separation as defined in claim 1, wherein the step of diverting water away from the electrophoretic area includes providing serrations on the edge of at least one thickened portion facing away from the electrophoretic area.

4. A process of electrophoretic separation as defined in claim 1, wherein the fluid is a member of the group consisting of solvent and buffer.

5. A process as defined in claim 1 wherein the water is separated from the thickened portions during electrophoresis.

6. In an electrophoresis plate including a generally flat layer of electrophoretic medium which includes a fluid, said electrophoretic medium having opposed first and second ends and an upper surface, an electrophoretic region being defined as the upper surface of the layer between the opposed ends, and wherein water is generated during electrophoresis, the improvement comprising:

means for diverting said generated water away from said electrophoretic region.

7. The electrophoresis plate as defined in claim 6 wherein the diverting means includes serrations, said serrations being provided at least at one of said opposed ends.

8. In an electrophoresis plate including a substrate which is chemically and electrically inert relative to electrophoretic separation, and a planar layer comprising an electrophoretic medium, the electrophoretic medium including a fluid, and a thickened portion provided on two opposing ends of said planar layer, forming an electrophoresis area between the two thickened portions, each of said thickened portions having an edge facing away from the electrophoresis area, the thickened portions including the elect ophoretic medium and fluid, the thickened portion functioning as a self-contained fluid reservoir for electrophoresis, the improvement comprising:

at least one of the thickened portions including means for diverting water separated during electrophoresis away from the electrophoresis area.

9. An electrophoresis plate as defined in claim 1, wherein the means for diverting water away from the electrophoresis area includes a hollow portion provided in the thickened portion.

10. An electrophoresis plate as defined in claim 1, wherein the means for diverting water away from the electrophoresis area includes serrations provided on the edge of the thickened portion facing away from the electrophoresis area.

11. An electrophoresis plate as defined in claim 1, wherein the fluid is a member of the group consisting of solvent and buffer.

12. An electrophoresis plate as defined in claim 1 wherein both of the thickened portions include means for diverting water away from the electrophoresis area.

* * * * *